(12) United States Patent  
Mohamed

(10) Patent No.: US 8,315,355 B2  
(45) Date of Patent: Nov. 20, 2012

(54) METHOD FOR OPERATING C-ARM SYSTEMS DURING REPEATED ANGIOGRAPHIC MEDICAL PROCEDURES

(75) Inventor: Ashraf Mohamed, Houston, TX (US)

(73) Assignee: Siemens Aktiengesellschaft, Munich (DE)

( * ) Notice: Subject to any disclaimer, the term of this patent is extended or adjusted under 35 U.S.C. 154(b) by 248 days.

(21) Appl. No.: 12/912,028

(22) Filed: Oct. 26, 2010

(65) Prior Publication Data

US 2011/0096907 A1 Apr. 28, 2011

Related U.S. Application Data

(60) Provisional application No. 61/255,543, filed on Oct. 28, 2009.

(51) Int. Cl.
*G01N 23/04* (2006.01)

(52) U.S. Cl. ........................................................ 378/62

(58) Field of Classification Search ................ 378/62, 378/98.11, 98.12; 382/128–132
See application file for complete search history.

(56) References Cited

OTHER PUBLICATIONS

W.H. Tang and A.C.S. Chung, entitled, "Cerebral Vascular Tree Matching of 3D-RA Data Based on Tree Edit Distance," Medical Imaging and Augmented Reality 2006, pp. 116-123, vol. 4091 of Lecture Notes in Computer Science, Springer Berlin / Heidelberg.

K.R. Hoffmann, A. Sen, L. Lan, K-G. Chua, J. Esthappan, M. Mazzucco, entitled "A System for Determination of 3D Vessel Tree Centerlines from Biplane Images," The International Journal of Cardiac Imaging 2000, pp. 315-330, vol. 16 (No. 5), Kluwer Academic Publishers/The Netherlands.

P. Noel, K.R. Hoffmann, A. M. Walczak, J. Dmochowski, entitled, "Registration of Vascular 3D Data Sets Obtained from Multiple-View Reconstructions," Computer Assisted Radiology and Surgery Jun. 2004, pp. 329-334, International Congress Series, vol. 1268, Elsevier.

V. Singh, L. Mukherjee, J. Xu, K.R. Hoffmann, G. Xu, Z. Chen, entitled, "Efficient Geometric Techniques for Reconstructing 3D Vessel Trees from Biplane Image," Proceedings of the Twenty-First Annual Symposium on Computational Geometry, 2005, pp. 368-369, ACM/Pisa, Italy.

C. Kirbas and F. Quek, entitled, "A Review of Vessel Extraction Techniques and Algorithms," ACM Computing Surveys, Jun. 2004, pp. 81-121, vol. 36 (No. 2), ACM.

F. Maes, D. Vandermeulen, P. Suetens, entitled, "Medical Image Registration Using Mutual Information," Proceedings of the IEEE, Oct. 2003, pp. 1699-1722, vol. 91 (No. 10), IEEE.

*Primary Examiner* — Courtney Thomas

(74) *Attorney, Agent, or Firm* — Donald B. Paschburg

(57) ABSTRACT

A method (100) for positioning and operating components (18, 22) of an X-ray C-arm system (10) during repeated angiographic medical procedures.

24 Claims, 6 Drawing Sheets

METHOD FOR OPERATING C-ARM SYSTEMS DURING REPEATED ANGIOGRAPHIC MEDICAL PROCEDURES

CROSS-REFERENCE TO RELATED APPLICATIONS

This application claims the benefit of Provisional U.S. Patent Application Ser. No. 61/255,543, entitled, "Method for Positioning of C-arm Systems during Repeated Angiographic Medical Procedures", filed in the name of Ashraf Mohamed on Oct. 28, 2009, the disclosure of which is also hereby incorporated herein by reference.

FIELD OF INVENTION

This invention relates to clinical X-ray angiography and, in particular, the acquisition of repeated or follow-up angiograms to, for example, assess the efficacy of treatment, or progression of a disease.

BACKGROUND OF THE INVENTION

An X-ray C-arm system is X-ray imaging apparatus that is used by healthcare professionals to obtain real-time images of internal structures of a patient, such as the vasculature. The imaging apparatus may be a rotational X-ray imaging device that acquires a series of 2D X-ray projections of the anatomical region of interest along an arced path. The type and configuration of the imaging apparatus varies but generally the rotation is accomplished by moving an X-ray source and an X-ray detector, mounted on respective ends of a rotatable C-shaped gantry, about a patient. The X-ray detector converts the raw X-ray projections into image data signals for subsequent image processing by the X-ray imaging system.

X-ray C-arm systems are routinely used in medicine during interventional medical procedures to acquire images for various reasons, for example: a) diagnostic examination of a patient's vascular structures, b) guidance of interventional therapeutic procedures such as stent placement, coiling of aneurysms, and embolization of arteriovenous malformations (AVMs), c) assessment of the efficacy of an interventional therapeutic procedure, and d) assessment of disease progression.

To diagnose, treat, and follow-up on vascular diseases, healthcare practitioners like radiologists use 2D and 3D angiography images to understand the structure and interconnections of a patient's vascular anatomy and the dynamic blood flow properties of the vasculature. 2D angiograms are X-ray projection images of vascular structures filled with contrast agent, which has been injected through a catheter. 3D angiograms can be obtained by rotating the X-ray C-arm around the patient, acquiring a set of angiograms as 2D projection images during the rotational run, and then reconstructing a 3D volume image from these set of projections. Digital subtraction angiography (DSA) is one of several techniques that can then be used to separate the imaged blood vessels from the surrounding anatomy. DSA specifically subtracts two X-ray images, one with and one without contrast injection. The background anatomy cancels out, and the contrasted vessel is highlighted.

Repeated acquisition of angiographic images for the same anatomical region is often necessary for treatment, and for follow-up procedures. For example, during an interventional medical procedure, it is usually important to compare the vessel anatomy and blood flow pattern before and after the insertion of a device, such as a coil or a stent, inside the patient's artery. Also, at the end of an interventional medical procedure, an angiographic image of the overall anatomical organ treated (e.g., left cerebral hemisphere) is required in order to compare the blood vessel anatomy and flow dynamics before and after the treatment. Also, repeated acquisition of angiographic images permits a comparison of the blood vessel morphology and blood flow pattern during a follow-up to a procedure or treatment in order to assess disease progression.

However, the generation of a 2D angiographic image that matches or closely matches another acquired at a previous time for these comparisons is often challenging. This is because slight variations in patient positioning on the radiographic table, differences in table height, translation, zoom setting, and C-arm angles may produce significantly different images. Using the state-of-the-art angiographic C-arm systems, the healthcare practitioner has to continuously apply X-ray fluoroscopy, while intermittently injecting angiographic contrast, in order to adjust the C-arm and table positions so that the resulting image visually matches a 2D angiographic image acquired at a previous time point. This subjects the patient to an additional dosage of X-rays, an additional dosage of contrast, and lengthens the procedure time. Since this approach depends on visual comparisons and manually-driven movements of components of the C-arm system, it is tedious and it often fails to produce a 2D image that accurately matches another acquired at a previous time point. Secondly, the patient's position on the radiographic table may be different between the initial angiogram and the second angiogram due to the acquisition of the two images on different days, or due to a patient's motion in between the two imaging times. The trouble in producing a 2D image that accurately matches a previously-acquired image may lead to the difficulty in assessing disease progression or the efficacy of treatment, since the two images being compared do not lend themselves to a point-to-point comparison.

Consequently, there is a need to overcome the limitations of state-of-the-art angiographic C-arm systems in allowing easy and fast acquisition of a 2D angiographic C-arm image that matches or substantially matches another image of the same anatomical region acquired at a previous time point. Further, there is a need of a method that allows straight forward comparison between two images of the same anatomical region generated at different times.

SUMMARY OF THE INVENTION

The above problems are obviated by the present invention which provides a method that generates an angiographic image of a subject using an X-ray C-arm imaging system, comprising calculating the parameters of the C-arm imaging system for producing a target image that at least substantially matches a source image; driving either or both a C-arm and a radiographic table of the C-arm imaging system to respective operating settings based on the calculated parameters; applying the image acquisition parameters to the C-arm imaging system based on the image acquisition parameters of the source image; and operating the C-arm imaging system to acquire the desired target image. The source image may be an image of the same anatomical region of the subject acquired at a previous imaging time. Alternatively, the source image may comprise a template for the anatomical region of the subject being imaged. The parameters may comprise positional settings for the C-arm and the table. The parameters may also comprise the positioning of an X-ray source and an X-ray detector of the C-arm imaging system relative to the imaged anatomical region of the subject at least substantially the same as the positioning during acquisition of the source image.

The calculating step may comprise calculating the at least substantially same projection geometry for the target image as the projection geometry for the source image. In such case, the calculating of the at least substantially same projection geometry may comprise substantially maintaining the angle of the C-arm with respect to the coordinate system of the subject and the distances between an X-ray source and an X-ray detector of the C-arm imaging system to the coordinate origin of the subject the same as during the acquisition of the source image. Alternatively, the calculating step may comprise calculating the at least substantially same projection geometry for the target image as the projection geometry for the source image using the transformation between the respective coordinate frames of the subject during the acquisitions of the source image and the target image, and the C-arm and the radiographic table positions during the acquisition of the source image. In such case, the calculating of the at least substantially same projection geometry may comprise substantially maintaining the angle of the C-arm with respect to the coordinate system of the subject and the distances between an X-ray detector and an X-ray source of the C-arm imaging system to the coordinate origin of the subject the same as during the acquisition of the source image using said transformation between the respective coordinate frames of the subject during the acquisitions of the source image and the target image, and said C-arm and radiographic table positions during the acquisition of the source image.

The calculating step may also comprise a) extracting 3D/2D projection geometry from a 2D projection source image to obtain a 2D/3D coordinate transformation; b) acquiring a first 3D angiographic image during the acquisition of the source image and a second 3D angiographic image during the acquisition of the target image; c) extracting respective 3D vessel skeletons from the 3D angiographic images; d) performing a 3D/3D registration of the extracted vessel skeletons to obtain a 3D/3D coordinate transformation from the registration; e) calculating a 3D/2D projection geometry based on the coordinate transformations; and f) estimating the parameters of the C-arm imaging system from the calculation of the 3D/2D projection geometry. The calculating step may alternatively comprise a) extracting 3D/2D projection geometry from a 2D projection source image to obtain a 2D/3D coordinate transformation from the extraction of the 3D/2D projection geometry; b) acquiring a first 2D biplane angiographic image during the acquisition of the source image and a second 2D biplane angiographic image during the acquisition of the target image; c) reconstructing respective 3D vessel skeletons from the 2D biplane angiographic images; d) performing a 3D/3D registration of the reconstructed vessel skeletons to obtain a 3D/3D coordinate transformation from the registration; e) calculating a 3D/2D projection geometry based on the coordinate transformations; and f) estimating the parameters of the C-arm imaging system from the calculation of the 3D/2D projection geometry. The calculating step may alternatively comprise a) extracting 3D/2D projection geometry from a 2D projection source image to obtain a 2D/3D coordinate transformation from the extraction of the 3D/2D projection geometry; b) acquiring a first 3D anatomical image during the acquisition of the source image and a second 3D anatomical image during the acquisition of the target image; c) performing a 3D/3D intensity-based registration of the anatomical images to obtain a 3D/3D coordinate transformation from the registration; d) calculating a 3D/2D projection geometry based on the coordinate transformations; and e) estimating the parameters of the C-arm imaging system from the calculation of the 3D/2D projection geometry.

The driving step may be performed automatically or manually. In the latter case, the driving may be performed manually using visual cues indicating the direction and magnitude of necessary movements by the C-arm and the radiographic table. The method may also comprise the additional step of generating a joint visualization of the target and source images. The joint visualization may be accomplished by displaying a side-by-side comparison of the source and target images; displaying an overlay of fused source and target images; or displaying a composite image resulting from a subtraction of the two images that allows the easy detection of small differences between the two images.

The present invention also provides a method for positioning X-ray C-arm apparatus during a repeated acquisition of an angiographic image for the same anatomical region of a subject, comprising establishing a relationship between the coordinate frames of the subject during the original and the repeated imaging times to determine the positioning of a C-arm and a subject support table of the apparatus for acquiring the repeated angiographic image. The establishing step may comprise acquiring additional images at the original and the repeated imaging times that contain 3D anatomical information that may be matched between the original and the repeated angiographic images. The establishing step may also comprise acquiring additional images at the original and the repeated imaging times that are used to construct 3D anatomical or vessel information that may be matched between the original and the repeated angiographic images.

The present invention further provides a method for operating an X-ray C-arm apparatus during acquisition of angiographic images for the same anatomical region of a plurality of subjects, comprising establishing a relationship between the coordinate frames of a template image of the anatomical region and a respective subject at imaging time to determine and implement the positioning of the C-arm apparatus for acquiring the angiographic image of the anatomical region of the respective subject.

The present invention further provides an X-ray imaging system, comprising an X-ray source that generates X-ray beams; an X-ray detector that is adapted to receive the X-ray beams; a support table positioned between the source and the detector such that the X-ray beams pass through a portion of the vasculature structure of a subject lying thereon and project onto the detector, said detector converting the raw X-ray projections into image data signals for subsequent processing; a rotatable C-arm gantry arrangement that has the source and the detector mounted on opposite ends thereof and that moves the source and the detector about the subject and the table in a coordinated manner so that the X-ray projections of the imaged portion of the vasculature structure can be generated from different angular directions; and a computer system which controls the operation of the system and its components and processes the image data obtained from the detector for display, storage, and/or other usage, said computer system positioning the C-arm and the table during a repeated acquisition of an angiographic image for the imaged portion of the vasculature structure based on the transformation between the respective coordinate frames of the subject during the two imaging times.

DESCRIPTION OF THE DRAWINGS

For a better understanding of the present invention, reference is made to the following description of an exemplary embodiment thereof, and to the accompanying drawings, wherein.

DETAILED DESCRIPTION

Figure 1:
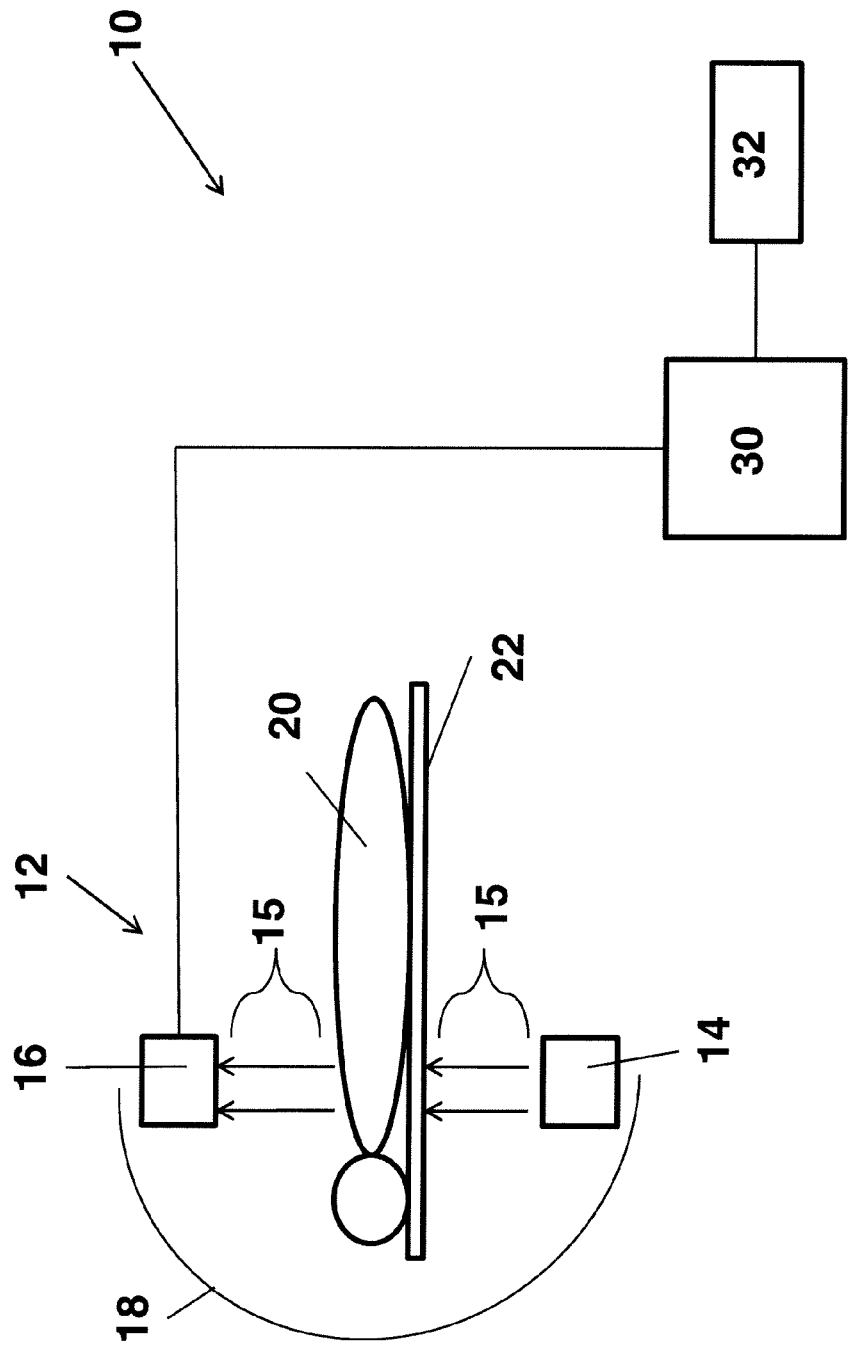
FIG. 1 shows a block diagram of an X-ray C-arm system operable in accordance with the present invention (simplified)

FIG. 1 is a block diagram of an X-ray C-arm imaging system 10 (simplified) that operates in accordance with the present invention. The system 10 comprises a rotational X-ray imaging apparatus 12 having an X-ray source 14 that generates X-ray beams 15 towards an X-ray detector 16. The X-ray source 14 and the X-ray detector 16 are mounted on opposite ends of, and coupled to one another via, a rotatable C-arm gantry arrangement 18. A patient to be imaged 20 is positioned on a radiographic support table 22 between the two components 14, 16 such that the X-ray beams 15 pass through the patient 20, and in particular, the anatomical area of interest, and project onto the X-ray detector 16. The detector 16 converts the raw X-ray projections into image data signals for subsequent processing by the C-arm system 10. As a result of the rotation of the C-arm 18, the X-ray source 14 and the X-ray detector 16 are moved about the patient 20 and the table 22 in a coordinated manner so that the X-ray projections of the vasculature structure of the patient 20 can be generated from different angular directions and a series of 2D X-ray projections of the anatomical area are acquired along an arced path.

The rotational X-ray imaging apparatus 12 is operably coupled to a computer system 30 which controls the operation of the C-arm system 10 and its components and processes the image data obtained from the X-ray detector 16 to transform them into a visual representation of the patient's vasculature structure (e.g., reconstructed images of the vasculature structure). In particular, the computer system 30 operates on the image data using well-known mathematical image processing and reconstruction algorithms/techniques as needed, such as segmentation, extraction, Fourier transforms, registration, etc., and generates for display, storage, and/or other usage corresponding X-ray images. The computer system 30 is also operably connected to appropriate user interfaces 32, like displays, storage media, input/output devices, etc.

The various components of the C-arm system 10 are conventional and well known components. However, the computer system 30 is adapted to permit the X-ray imaging system 10 to operate and to implement methods in accordance with the present invention. In particular, the computer system 30 may operate the system 10 utilizing appropriate application software and algorithms that incorporate and carry out the methods.

Figure 2:
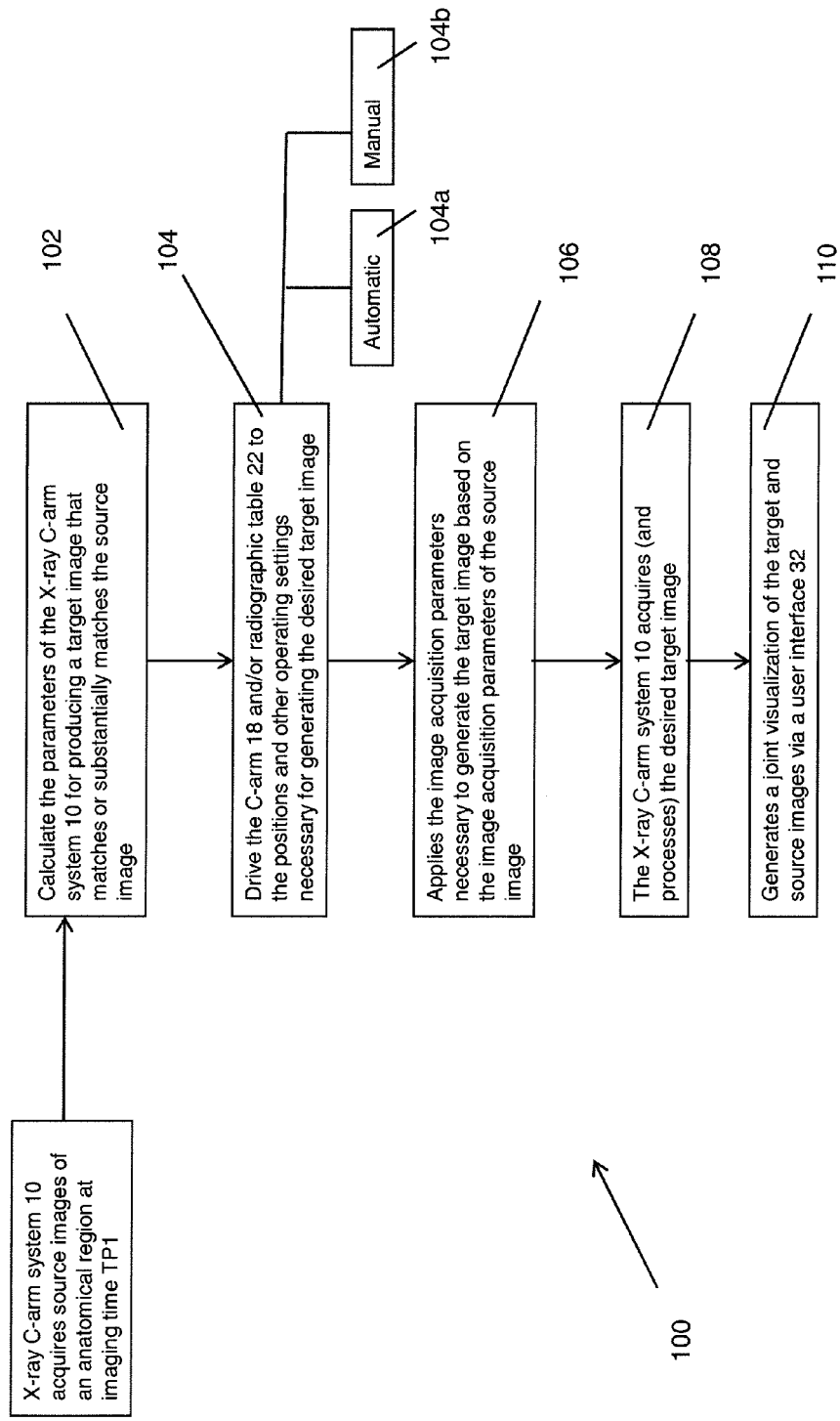
FIG. 2 show a flow chart of a method implemented in accordance with the present invention.

FIG. 2 show a flow chart of a method 100 carried out in accordance with the present invention. In describing the method 100 shown in the various figures, X-ray images acquired during a first angiographic study are identified by a label TP1 (imaging Time Point 1), and those acquired during a second angiographic study for the same patient and same anatomical region are identified by a label TP2 (imaging Time Point 2). The method 100 may utilize any one of the images typically acquired and processed by the C-arm system 10 during an angiographic study, including for example, 2D angiograms (subtracted or non-subtracted), 3D DSA, 3D anatomical images, and biplane 2D DSA angiograms. As indicated above, the goal of the method 100 is to generate, for example, a TP2 2D angiogram (referred to below more generally as the target image) that shows the blood vessels at the same or substantially same orientation and appearance as a TP1 2D angiogram (referred to below more generally as the source image).

Prior to carrying out the method 100, a healthcare professional operates the C-arm system 10 to acquire TP1 source images of vascular structures of interest of the patient 20. At some time period thereafter, the healthcare professional operates the C-arm system 10 in accordance with the method 100 to acquire TP2 target images of the same anatomical region (i.e., to repeat or substantially repeat the acquisition of the TP1 source images). The method 100 first calculates the parameters of the C-arm system 10 for producing a target image that matches or substantially matches a source image (Step 102). These parameters particularly include the typical operating and positional settings for the C-arm 18 and the radiographic table 22, such as radiographic table 22 height, zoom setting, C-arm 18 angles, etc. This is more fully described below. The method 100 uses the calculated parameters to drive the C-arm 18 and/or radiographic table 22 to the positions and other operating settings necessary for generating the desired target image (Step 104). Depending upon the type of C-arm system 10 available and/or the operating protocol, this can be done automatically (Step 104*a*) or manually (Step 104*b*). The manual operation may be guided by visual cues indicating the direction and magnitude of necessary movements by the C-arm 18 and/or radiographic table 22.

The method 100 then applies the image acquisition parameters (e.g., X-ray energy of the imaging apparatus) necessary to generate the desired target image based on the image acquisition parameters of the source image (Step 106). After the C-arm system 10 acquires (and processes) the desired target image (Step 108), the method 100 generates a joint visualization of the target and source images (Step 110). This can be accomplished in several ways, for example, a) side-by-side comparison via a linked cursor; b) overlay of fused images; or c) subtraction of the two images in order to generate a composite image that allows the easy detection of small differences between the two images. The joint visualization is presented via a monitor, or other user interface 32, to the healthcare professional. The user interface 32 includes the linked cursor (generated and directed, for example, via a respective computer mouse) and other appropriate input/output devices for studying and manipulating the joint visualization.

Figure 3:
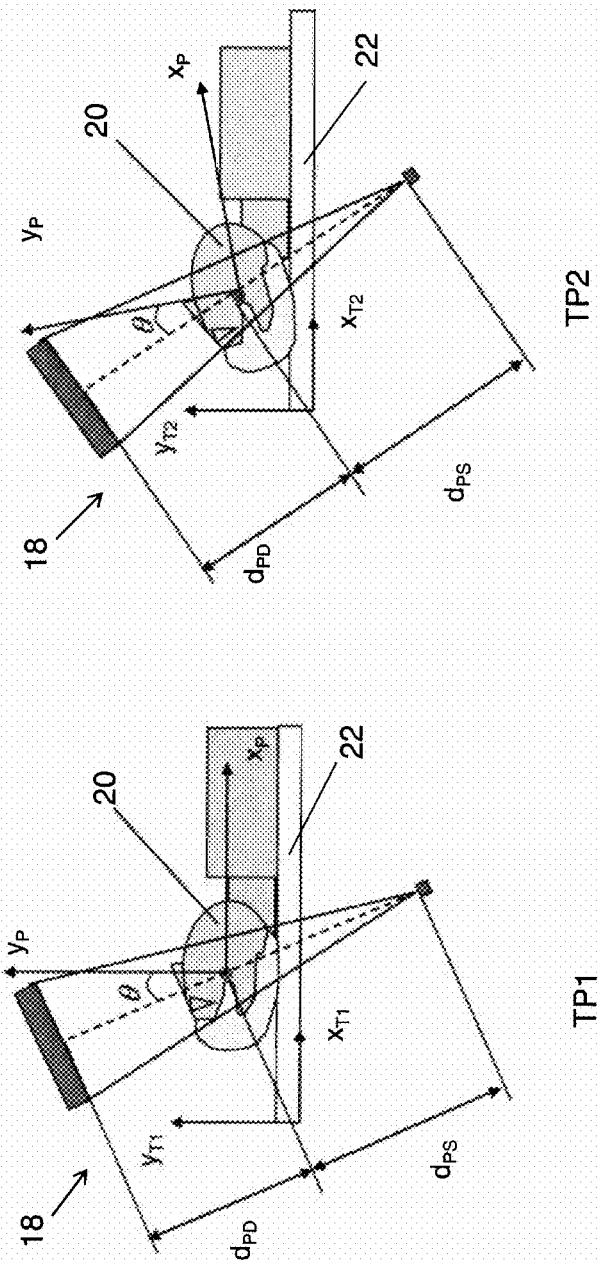
FIG. 3 shows a graphical representation of projection geometry of an X-ray C-arm system at two imaging time points.

As noted above, the method 100 calculates the parameters of the C-arm system 10 for producing a target image that matches or substantially matches a source image (Step 102). Generally, a key to the successful generation of the desired TP2 target image is to position the X-ray source 14 and the detector 16 relative to the imaged anatomical region of the patient 20 in exactly, or at least substantially, the same way as they were positioned during acquisition of the TP1 source image. This approach is better understood by the 2D illustration in FIG. 3. In order to obtain a target image at TP2 with the same, or substantially the same, projection geometry as the source image at TP1, the method 100 maintains (a) the angle θ of the C-arm 18 with respect to the patient's 20 coordinate system $x_P$, $y_P$ and (b) the distances $d_{PD}$, $d_{PS}$ between the X-ray detector 16 and the X-ray source 14 to the patient's 20 coordinate origin. The figure shows the projection geometry at TP2 as slightly askew from the projection geometry at TP1. Knowing the relationship or transformation between the coordinate frames $x_P$, $y_P$ of the patient 20 at the imaging times TP1 and TP2, and the table 22 and C-arm 18 positions used during acquisition of the source image at TP1, the method 100 computes the necessary C-arm 18 position and angles, and table 22 position needed to generate the desired target image at TP2 using conventional mathematical techniques. Note that the table's 22 coordinate system at TP1 is denoted as $x_{T1}$, $y_{T1}$ and at TP2 as $x_{T2}$, $y_{T2}$.

Even though information of the C-arm 18 angles and the table 22 position at TP1 may be already recorded in the header of the source image file (e.g., DICOM format header) and accessible by the computer system 30, the method 100 recognizes that any patient motion in between the two imaging times TP1 and TP2 may work against using the stored C-arm 18 and table 22 parameters and not result in a target image that reproduces the same or substantially same image content in the source image. The method 100 instead establishes a relationship between the coordinate frames of the patient 20 at the imaging times TP1 and TP2 to determine the C-arm 18 angles and the table 22 position that should be used for generating desired the target image.

Figure 4:
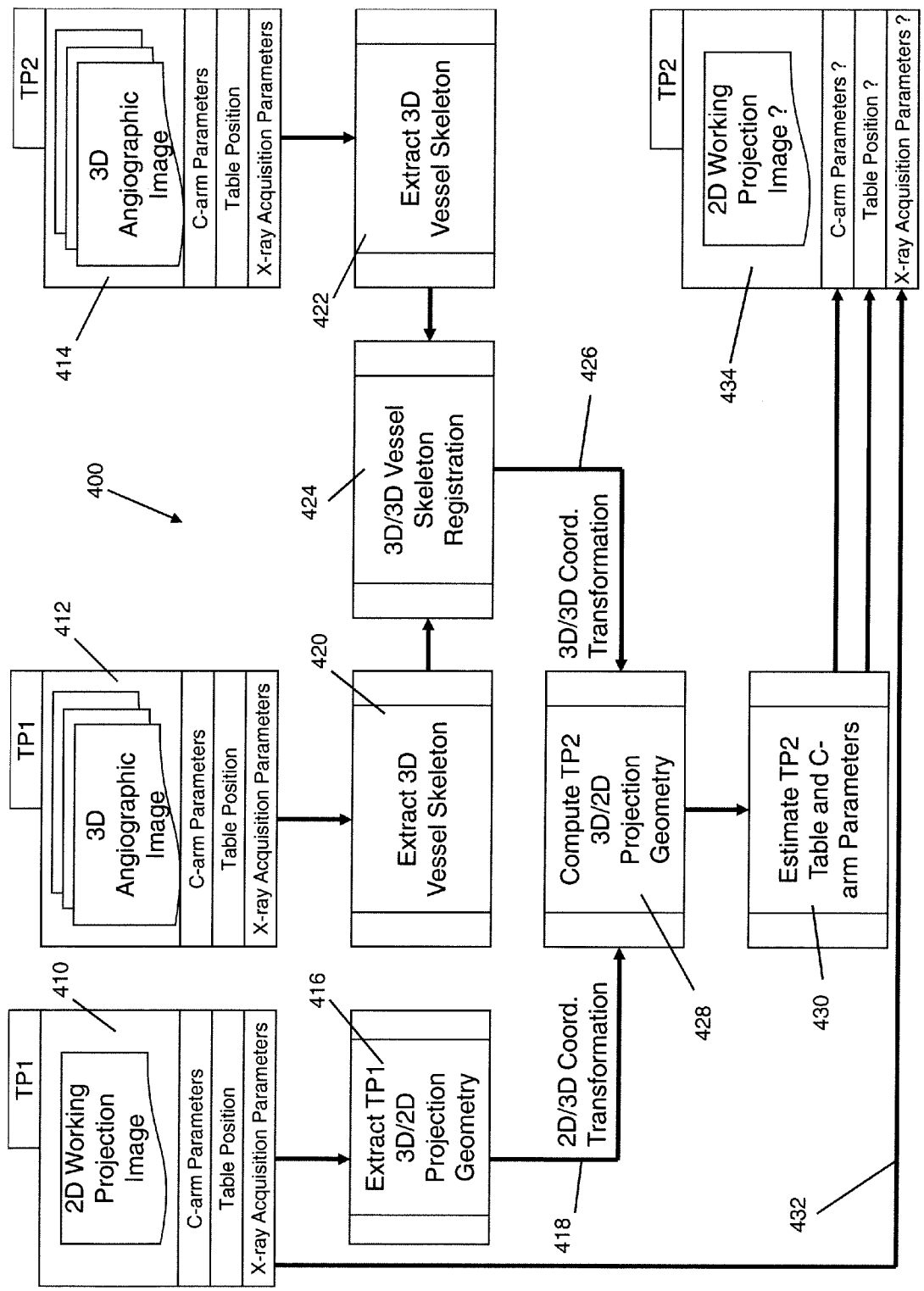
FIG. 4 shows a first method of calculating parameters of an X-ray C-arm system as per the method of FIG. 2.
Figure 5:
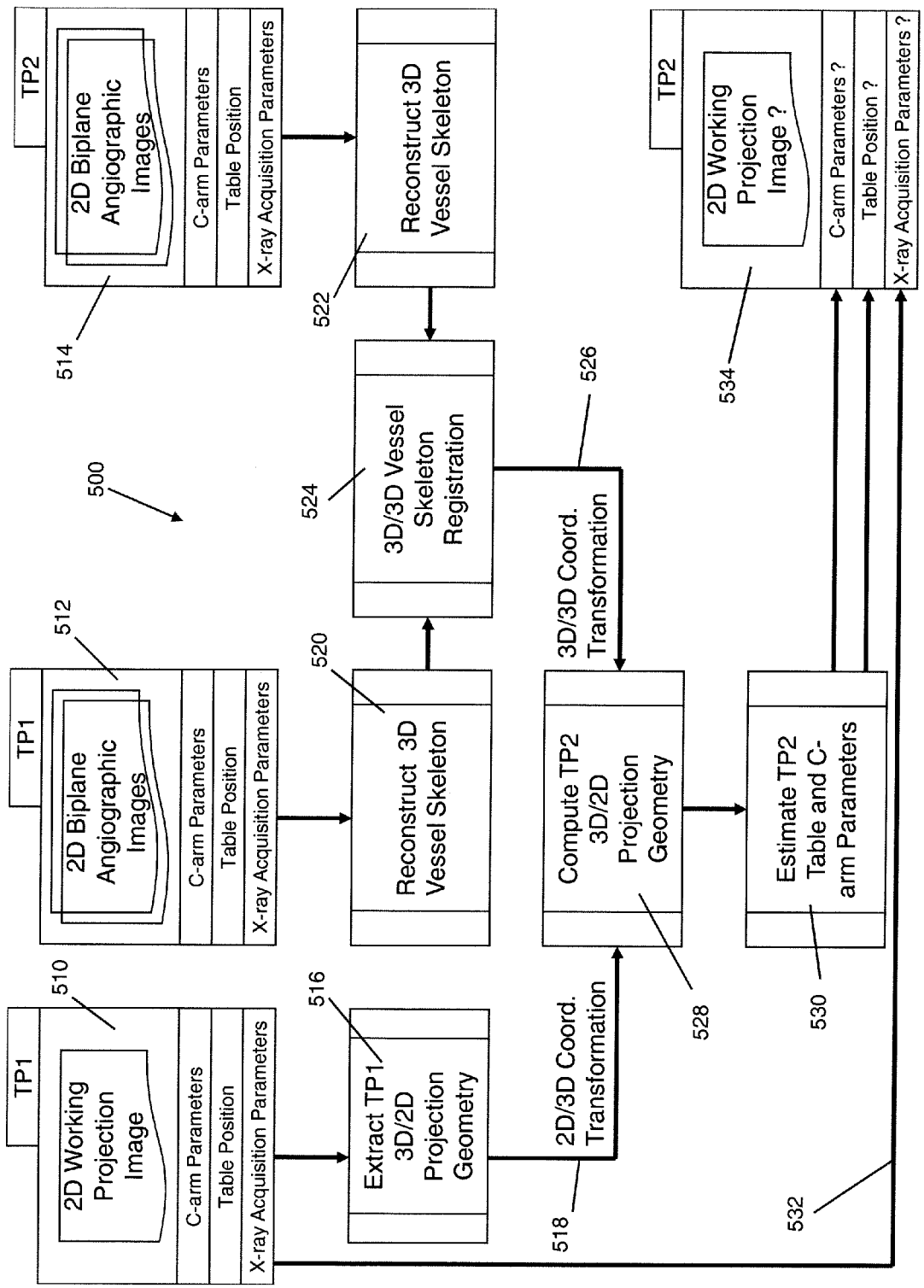
FIG. 5 shows a second method of calculating parameters of an X-ray C-arm system as per the method of FIG. 2.
Figure 6:
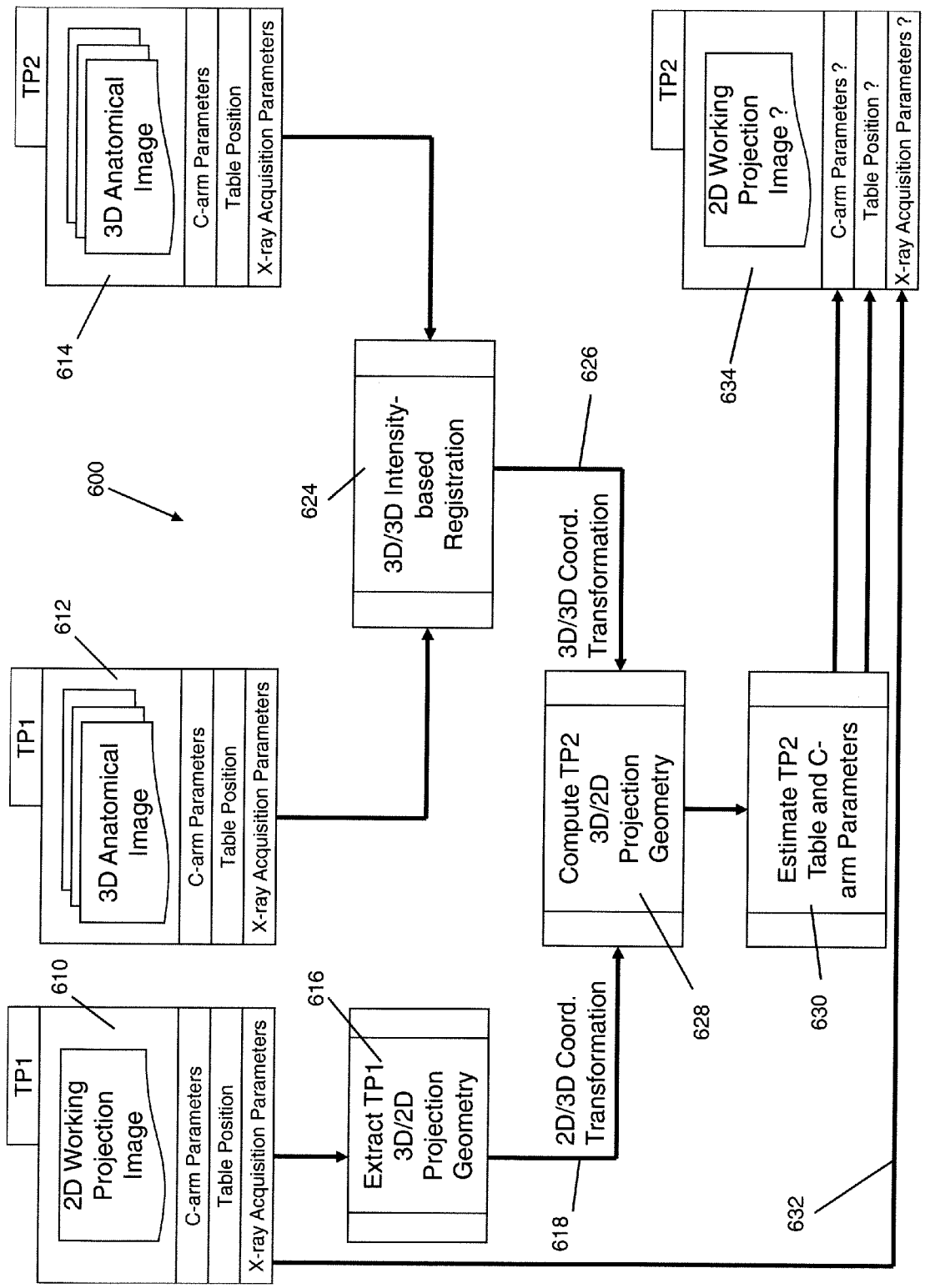
FIG. 6 shows a third method of calculating parameters of an X-ray C-arm system as per the method of FIG. 2.

There are several ways in which the relationship or transformation between the patient's 20 coordinate frames at imaging times TP1 and TP2 may be obtained. FIGS. 4, 5, and 6 illustrate a number of such clinically feasible methodologies or scenarios. In each of these scenarios, and in general, the method 100 acquires additional images at imaging times TP1 and TP2. These additional images either (a) contain 3D anatomical information that may be matched between the source and target images, or (b) may be used to construct 3D anatomical or vessel information that could be matched between the images.

FIG. 4 shows a first method 400 in which a 2D working projection image of the vascular structure of interest 410 (source image) is obtained at imaging time TP1 and an additional 3D angiographic (3D DSA) image 412 is obtained at imaging time TP1. The 3D DSA image is routinely acquired at the beginning of an interventional medical procedure, or a follow-up angiographic study. The method 100 extracts (i.e., separates from the surrounding vasculature) TP1 3D/2D projection geometry 416 from the source image 410. This results in a 2D/3D coordinate transformation 418. The method 100 also extracts a 3D skeleton of the vessels from the 3D angiography image 420. These latter steps may be performed at imaging time TP1 or later. At imaging time TP2, another additional 3D angiographic (3D DSA) image 414 is obtained. The method 100 extracts a 3D skeleton of the vessels from the second 3D angiography image 422 and then performs a 3D/3D registration of the extracted vessels 424 (i.e. comparison of the extracted vessels). This results in a 3D/3D coordinate transformation 426, which is used in conjunction with knowledge of the projection geometry of the source image 410 (i.e., the 2D/3D coordinate transformation 418) to calculate the TP2 3D/2D projection geometry 428 and estimate the necessary table 22 and C-arm 18 TP2 parameters 430. As noted above, the method 100 uses the estimated parameters to drive the table 22 and the C-arm 18 to their positions (not shown) and applies the TP1 image acquisition parameters 432 of the source image 410. The C-arm system 10 then acquires at imaging time TP2 the matching (or substantially matching) 2D working projection image of the vascular structure of interest obtained at imaging time TP1, i.e., the desired target image 434.

FIG. 5 shows a second method 500 in which a 2D working projection image of the vascular structure of interest 510 (source image) is obtained at imaging time TP1 and an additional 2D biplane angiographic image 512 is obtained at imaging time TP1. The 2D biplane angiographic image is routinely acquired at the beginning of an interventional medical procedure, or a follow-up angiographic study. The method 100 extracts (i.e., separates from the surrounding vasculature) TP1 3D/2D projection geometry 516 from the source image 510. This results in a 2D/3D coordinate transformation 518. The method 100 also reconstructs a 3D skeleton of the vessels from the 2D biplane angiographic image 520. These latter steps may be performed at imaging time TP1 or later. At imaging time TP2, another additional 2D biplane angiographic image 514 is obtained. The method 100 reconstructs a 3D skeleton of the vessels from the second 2D biplane angiographic image 522 and then performs a 3D/3D registration of the reconstructed vessels 524 (i.e. comparison of the reconstructed vessels). This results in a 3D/3D coordinate transformation 526, which is used in conjunction with knowledge of the projection geometry of the source image 510 (i.e., the 2D/3D coordinate transformation 518) to calculate the TP2 3D/2D projection geometry 528 and estimate the necessary table 22 and C-arm 18 TP2 parameters 530. As noted above, the method 100 uses the estimated parameters to drive the table 22 and the C-arm 18 to their positions (not shown) and applies the TP1 image acquisition parameters 532 of the source image 510. The C-arm system 10 then acquires at imaging time TP2 the matching (or substantially matching) 2D working projection image of the vascular structure of interest obtained at imaging time TP1, i.e., the desired target image 534.

FIG. 6 shows a third method 600 in which a 2D working projection image of the vascular structure of interest 610 (source image) is obtained at imaging time TP1 and an additional 3D anatomical image 612 are obtained at imaging time TP1. The 3D anatomical images may be acquired by state-of-the-art angiographic C-arm systems, and is also known by trade/brand names, such as "Cone-beam CT", "C-arm CT", "dyna CT", "Xper CT", and "Innova CT". The method 100 extracts (i.e., separates from the surrounding vasculature) TP1 3D/2D projection geometry 616 from the source image 610. This results in a 2D/3D coordinate transformation 618. These latter steps may be performed at imaging time TP1 or later. At imaging time TP2, another additional 3D anatomical image 614 is obtained. The method 100 then performs a 3D/3D intensity-based registration of the images 624 (i.e. comparison of the images). This results in a 3D/3D coordinate transformation 626, which is used in conjunction with knowledge of the projection geometry of the source image 610 (i.e., the 2D/3D coordinate transformation 618) to calculate the TP2 3D/2D projection geometry 628 and estimate the necessary table 22 and C-arm 18 TP2 parameters 630. As noted above, the method 100 uses the estimated parameters to drive the table 22 and the C-arm 18 to their positions (not shown) and applies the TP1 image acquisition parameters 632 of the source image 610. The C-arm system 10 then acquires at imaging time TP2 the matching (or substantially matching) 2D working projection image of the vascular structure of interest obtained at imaging time TP1, i.e., the desired target image 634.

As described above, the present invention provides a method 100 that controls and adjusts the C-arm 18 and radiographic table 22 of an angiographic system 10 in order to generate a target image that matches or substantially matches a source image acquired for the same patient at a previous time point. However, the method 100 may also be used to generate the C-arm system 10 parameters necessary for generating angiographic 2D images of the same anatomical region but for different patients in a standard orientation. Today, images are typically acquired and studied for AP (anterior-posterior) or Lateral positions. Small variations in the patient's positioning on the radiographic table 22 lead to images of the same anatomical region generated for different patients likely having slightly different appearances of the imaged blood vessels. However, using the method 10 described above, it is possible to acquire 2D images from different patients in standard projection angles that are less dependent on the operator of the angiographic system 10. This may be performed by aligning each imaged patient's 3D anatomical region to a template or atlas of the vasculature, rather than aligning relative to a first time point TP1 as described herein. This will enable the statistical and comparative analysis of 2D vascular images across a group of individuals.

Other modifications are possible within the scope of the invention. For example, the subject to be scanned may be an animal subject or any other suitable object rather than a human patient. Also, the C-arm system 10 has been described in a simplified fashion and may be constructed in various well-known manners and using various well-known components. For example, the computer system 30 may incorporate the control portions of the various system 10 components or may be modularly constructed with separate but coordinated units, such as an image processing unit, user interfaces, workstations, etc. Also, although the steps of each method have been described in a specific sequence, the order of the steps may be re-ordered in part or in whole and the steps may be modified, supplemented, or omitted as appropriate.

Also, the C-arm system 10 and the computer system 30 may use various well known algorithms and software applications to implement the processing steps and substeps, such as extraction, segmentation, projection geometry computation, image reconstruction, image registration, etc. Further, the method 100 may be implemented in a variety of algorithms and software applications. Further, the method 100 may be supplemented by additional processing steps or techniques to remove resulting image artifacts, provide a sufficient number of image frames, or, otherwise, insure reliable blood vessel image generation.

What is claimed is:

1. A method of generating an angiographic image of a subject using an X-ray C-arm imaging system, comprising:
   a. calculating parameters of the C-arm imaging system for producing a target image that at least substantially matches a source image;
   b. driving either or both a C-arm and a radiographic table of the C-arm imaging system to respective operating settings based on the calculated parameters;
   c. applying image acquisition parameters to the C-arm imaging system based on the image acquisition parameters of the source image; and
   d. operating the C-arm imaging system to acquire the target image.

2. The method of claim 1, wherein the source image comprises an image of the same anatomical region of the subject acquired at a previous imaging time.

3. The method of claim 1, wherein the parameters comprise positional settings for the C-arm and the table.

4. The method of claim 1, wherein the parameters comprise the positioning of an X-ray source and an X-ray detector of the C-arm imaging system relative to the imaged anatomical region of the subject at least substantially the same as the positioning during acquisition of the source image.

5. The method of claim 1, wherein said calculating comprises calculating the at least substantially same projection geometry for the target image as the projection geometry for the source image.

6. The method of claim 5, wherein said calculating the at least substantially same projection geometry comprises substantially maintaining the angle of the C-arm with respect to the coordinate system of the subject and the distances between an X-ray source and an X-ray detector of the C-arm imaging system to the coordinate origin of the subject the same as during the acquisition of the source image.

7. The method of claim 1, wherein said calculating comprises calculating the at least substantially same projection geometry for the target image as the projection geometry for the source image using the transformation between the respective coordinate frames of the subject during the acquisitions of the source image and the target image, and the C-arm and the radiographic table positions during the acquisition of the source image.

8. The method of claim 7, wherein said calculating the at least substantially same projection geometry comprises substantially maintaining the angle of the C-arm with respect to the coordinate system of the subject and the distances between an X-ray detector and an X-ray source of the C-arm imaging system to the coordinate origin of the subject the same as during the acquisition of the source image using said transformation between the respective coordinate frames of the subject during the acquisitions of the source image and the target image, and said C-arm and radiographic table positions during the acquisition of the source image.

9. The method of claim 1, wherein said calculating comprises:
   a. extracting 3D/2D projection geometry from a 2D projection source image to obtain a 2D/3D coordinate transformation;
   b. acquiring a first 3D angiographic image during the acquisition of the source image and a second 3D angiographic image during the acquisition of the target image;
   c. extracting respective 3D vessel skeletons from the 3D angiographic images;
   d. performing a 3D/3D registration of the extracted vessel skeletons to obtain a 3D/3D coordinate transformation from the registration;
   e. calculating a 3D/2D projection geometry based on the coordinate transformations; and
   f. estimating the parameters of the C-arm imaging system from the calculation of the 3D/2D projection geometry.

10. The method of claim 1, wherein said calculating comprises
   a. extracting 3D/2D projection geometry from a 2D projection source image to obtain a 2D/3D coordinate transformation from the extraction of the 3D/2D projection geometry;
   b. acquiring a first 2D biplane angiographic image during the acquisition of the source image and a second 2D biplane angiographic image during the acquisition of the target image;
   c. reconstructing respective 3D vessel skeletons from the 2D biplane angiographic images;
   d. performing a 3D/3D registration of the reconstructed vessel skeletons to obtain a 3D/3D coordinate transformation from the registration;
   e. calculating a 3D/2D projection geometry based on the coordinate transformations; and f. estimating the parameters of the C-arm imaging system from the calculation of the 3D/2D projection geometry.

11. The method of claim 1, wherein said calculating comprises a. extracting 3D/2D projection geometry from a 2D projection source image to obtain a 2D/3D coordinate transformation from the extraction of the 3D/2D projection geometry;

b. acquiring a first 3D anatomical image during the acquisition of the source image and a second 3D anatomical image during the acquisition of the target image;

c. performing a 3D/3D intensity-based registration of the anatomical images to obtain a 3D/3D coordinate transformation from the registration;

d. calculating a 3D/2D projection geometry based on the coordinate transformations; and e. estimating the parameters of the C-arm imaging system from the calculation of the 3D/2D projection geometry.

12. The method of claim 1, wherein said driving is performed automatically.

13. The method of claim 1, wherein said driving is performed manually.

14. The method of claim 1, wherein said driving is performed manually using visual cues indicating the direction and magnitude of necessary movements by the C-arm and the radiographic table.

15. The method of claim 1, further comprising generating a joint visualization of the target and source images.

16. The method of claim 15, wherein the joint visualization comprises displaying a side-by-side comparison of the source and target images.

17. The method of claim 15, wherein the joint visualization comprises displaying an overlay of fused source and target images.

18. The method of claim 15, wherein the joint visualization comprises displaying a composite image resulting from a subtraction of the two images that allows the easy detection of small differences between the two images.

19. The method of claim 1, wherein the source image comprises a template for the anatomical region of the subject being imaged.

20. A method for positioning X-ray C-arm apparatus during a repeated acquisition of an angiographic image for the same anatomical region of a subject, comprising establishing a relationship between the coordinate frames of the subject during original and repeated imaging times to determine a positioning of a C-arm and a subject support table of the apparatus for acquiring the repeated angiographic image.

21. The method of claim 20, wherein said establishing comprises acquiring additional images at the original and the repeated imaging times that contain 3D anatomical information that are matched between the original and the repeated angiographic images.

22. The method of claim 20, wherein said establishing comprises acquiring additional images at the original and the repeated imaging times that are used to construct 3D anatomical or vessel information that are matched between the original and the repeated angiographic images.

23. A method for operating an X-ray C-arm apparatus during acquisition of angiographic images for the same anatomical region of a plurality of subjects, comprising establishing a relationship between the coordinate frames of a template image of the anatomical region and a respective subject at an imaging time to determine and implement a positioning of the C-arm apparatus for acquiring the angiographic image of the anatomical region of the respective subject.

24. An X-ray imaging system, comprising an X-ray source that generates X-ray beams; an X-ray detector that is adapted to receive the X-ray beams; a support table positioned between the source and the detector such that the X-ray beams pass through a portion of the vasculature structure of a subject lying thereon and project onto the detector, said detector converting the raw X-ray projections into image data signals for subsequent processing; a rotatable C-arm gantry arrangement that has the source and the detector mounted on opposite ends thereof and that moves the source and the detector about the subject and the table in a coordinated manner so that the X-ray projections of the imaged portion of the vasculature structure can be generated from different angular directions; and a computer system which controls the operation of the system and its components and processes the image data obtained from the detector for display, storage, and/or other usage, said computer system positioning the C-arm and the table during a repeated acquisition of an angiographic image for the imaged portion of the vasculature structure based on a transformation between respective coordinate frames of the subject during two imaging times.

* * * * *